United States Patent

Jacobs et al.

[11] Patent Number: 5,525,514
[45] Date of Patent: Jun. 11, 1996

[54] WASH DETECTION METHOD FOR DRIED CHEMISTRY TEST ELEMENTS

[75] Inventors: Merrit N. Jacobs, Fairport, N.Y.; Russel H. Marvin, Riverton, Wyo.; Paul J. Mulqueen, Fairport, N.Y.

[73] Assignee: Johnson & Johnson Clinical Diagnostics, Inc., Rochester, N.Y.

[21] Appl. No.: 415,262

[22] Filed: Apr. 3, 1995

Related U.S. Application Data

[63] Continuation-in-part of Ser. No. 224,021, Apr. 6, 1994, abandoned.

[51] Int. Cl.⁶ .................................................. G01N 33/543
[52] U.S. Cl. ............................ 436/46; 422/64; 422/67; 422/82.05; 436/43; 436/50; 436/55; 436/164; 436/177; 436/805
[58] Field of Search ............................ 436/43, 46, 49, 436/50, 54, 55, 164, 166, 174, 805, 44, 177; 422/63, 64, 65, 66, 67, 105, 119, 82.05

[56] References Cited

U.S. PATENT DOCUMENTS

| | | | |
|---|---|---|---|
| 3,992,158 | 11/1976 | Przybylowicz et al. | 23/253 TP |
| 4,420,566 | 12/1983 | Jessop et al. | 436/46 |
| 4,517,288 | 5/1985 | Giegel et al. | 435/7 |
| 4,627,014 | 12/1986 | Lo et al. | 364/571 |
| 5,037,613 | 8/1991 | Shaw et al. | 422/64 |
| 5,049,359 | 9/1991 | Azuma et al. | 422/67 |
| 5,049,487 | 9/1991 | Phillips et al. | 435/4 |
| 5,084,620 | 1/1992 | Butturini | 250/338.5 |
| 5,174,960 | 12/1992 | Shaw et al. | 422/63 |
| 5,196,168 | 3/1993 | Muszak et al. | 422/64 |
| 5,281,395 | 1/1994 | Markart et al. | 422/82.05 |

FOREIGN PATENT DOCUMENTS 61-62865  9/1984  Japan.

*Primary Examiner*—Jill Warden
*Assistant Examiner*—Long V. Le
*Attorney, Agent, or Firm*—Dana M. Schmidt

[57] ABSTRACT

A method for verifying the effectiveness of a washing operation on a clinical dry chemistry slide element in which wash liquid is dispensed onto the surface of the slide element and then detection devices are used to verify the effectiveness of the wash by making an initial detection at an on center site followed by making a second detection at a second and off-center radial position. A comparison of the two readings provides verification of the wash. In addition, rate measurements can be made at each of the read positions to measure the effectiveness of the wash and to verify sample application for immunological assays.

6 Claims, 7 Drawing Sheets

WASH DETECTION METHOD FOR DRIED CHEMISTRY TEST ELEMENTS

RELATED APPLICATIONS

This is a continuation-in-part application of U.S. Ser. No. 224,021 filed on Apr. 6, 1994, now abandoned.

BACKGROUND OF THE INVENTION

In certain clinical diagnostic analyzers, dry analytical slide elements are utilized for immunorate chemistry assays. Examples of such elements include those manufactured by Eastman Kodak Company under the registered trademark EKTACHEM®.

Typical dry chemistry test elements, have a porous spreading layer containing antibodies immobilized therein that act as adsorption sites for an analyte of interest, such as a drug (D) and a chemical label (L); for example, a conjugate of the drug and a detectable species such as an enzyme. Typically, a sample containing drug (D) is applied to the spreading layer as a spot from a point source, such as a pipette tip. The sample quickly penetrates the pores of the spreading layer and simultaneously reconstitutes (dissolves) the chemical label (L) which has been previously coated onto the top of the spreading layer or applied as a separate solution. Alternatively, the chemical label can be added to the sample and the mixture applied to the element. Ideally, the label L becomes uniformly distributed in the liquid sample regardless of how it is applied. Thus, when the sample application process is complete, the spreading layer is saturated with a uniform layer of D & L. Because immobilized antibody is present throughout the spreading layer, D & L begin to bind to these adsorption sites. In order to detect the level of D present in the sample, there must be a competition between D & L for the limited number of antibody adsorption sites in the layer. That is, the amount of D is determined from its relative ability to compete against L for adsorption sites available in the spreading layer.

In an alternative type of immunological assay, commonly referred to as a sandwich assay, an antibody is contacted with a sample containing an analyte or drug (D) to cause the analyte to bind to the antibody. This complex is then contacted with a labeled antibody which reacts with the bound analyte. The amount of bound labeled antibody is thus directly proportional to the amount of bound analyte.

To measure D's success in competing for antibody sites, the amount of L bound to antibody is measured. Unfortunately, the differences between bound and unbound label (L) can not be distinguished, other than the fact that bound label is immobilized. Therefore, to measure the amount of L bound to the immobilized antibody, the L in solution has to be washed away from the region to be read by the detection device, such as an optical reflectometer, to determine the amount of D present by sensing the presence of L. This defines the need for a wash step or operation included in the assay procedure to facilitate the removal of unbound label from the detection read area of a slide element. Typically, this wash step is carried out in conventional immunoassays by applying about 30 to 100 microliters of wash liquid to the center of the area where the sample was spotted. As the wash liquid flows into the spreading layer, it displaces (pushes) the sample fluid containing dissolved and unbound L outward.

It has been found that conventional dispensing techniques, in which wash liquid is metered or dispensed directly to the center of the sample spot, fail to follow the idealized format above. Instead, wash liquid enters and traverses along the test element top surface and unbound label is washed out, primarily in the annular region of the spreading layer just below the contact line of the fluid meniscus (lens) created by the wash fluid on the top surface of the spreading layer. Consequently, this has been found to leave a significant fraction of unbound L in the center of the spot.

An improved wash technique is described in commonly assigned U.S. Ser. No. 880,902, filed 6 May 1992, now abandoned, in which wash liquid is applied by conventional means at a position in between the center of the sample spot and the inner periphery of the area wetted by the sample. Applying wash liquid in this manner allows the central portion of the original sample spot to be adequately washed of unbound label, while excess label at the periphery will not be redistributed back towards the center. In this way, a smaller volume of wash fluid (typically, about 10 to 13 uL) is required to push unbound L from the detection read area of the test element.

In any event, it is known that an insufficient wash volume, regardless of where it is applied, will fail to push the unbound label from the detection read area of an element, thereby producing undesirable and inaccurate test results.

Current means for verifying a wash operation include the use of wetness detectors which can generally sense the placement of a liquid onto the dried chemistry portion of a test slide element. This type of apparatus, an example of which is described in U.S. Pat. No. 5,084,620, is quite useful for indicating whether a premature wetness of a dried chemistry test element has occurred prior to sample dispensing, but inadequate otherwise in that it merely provides general qualitative determinations on a prewetted element, and not quantitative determinations.

Alternately, pressure transducers can be used to describe the presence of liquid on a test element. However, these devices are similarly limited and can only provide general information that a liquid has been applied and are not particularly effective to verify the success or failure of a wash sequence.

Therefore, there is a need to provide a means for verifying a wash process which will provide increased confidence that an adequate wash volume has been dispensed to displace unbound label from the read area of the slide element.

SUMMARY OF THE INVENTION

The present invention solves the stated need by providing a method of verifying a wash operation performed on a test element, such as for immunological assays.

In one aspect of the invention, there is disclosed a method for verifying a proper washing sequence on a test element having a chemistry portion of at least one reagent layer disposed thereon, the method comprising the steps of:

a) adding a wash liquid to the test element at a first wash position located within the chemistry portion;

b) reading the test element at a first read position located within the chemistry portion to detect a wash-influenced result;

c) reading the test element at a second read location within the chemistry portion that is different from the first read location, to detect a wash-influenced result, d) comparing the readings of steps b) and c); and e) discarding the results of the test if the reading of step b) is higher than the reading of step c) beyond normal noise variability.

An advantageous feature of the present invention is that by reading to detect a wash-influenced result, such as the displacement of unbound label at two specific locations within the chemistry portion of a test slide, and using conventionally known detection means such as commonly found on a clinical diagnostic analyzer, such as a reflectometer to determine optical density differences, a comparison of the two specific readings will provide immediate verification of the wash process and will reduce the probability of test error.

A further advantageous feature of the present invention is that since this detection method verifies unbound label has moved beyond the read detection area of the slide element, it is also able to detect any defect which restricts the flow of the unbound label from the read area; such as a bound sample matrix on the slide element or an improperly positioned wash tip.

A still further advantageous feature of the present invention is that the verification method provides an indirect indication of poor sample application onto a slide element.

Other advantageous features will become apparent from the following Description of Preferred Embodiments, when read in light of the attached drawings.

DESCRIPTION OF THE PREFERRED EMBODIMENTS

The invention is hereinafter described in the context of the preferred embodiments. Though these embodiments relate particularly to the verification of the wash operation of immunological assays, it can be readily seen that the described measurement technique is equally applicable to verifying the displacement of any dispensed liquid, including patient sample.

Terms such as "up", "down", "lower", "vertical", "horizontal", and "bottom" as used herein refer to the orientation of parts when the apparatus is positioned in its customary position of use.

Figure 1:
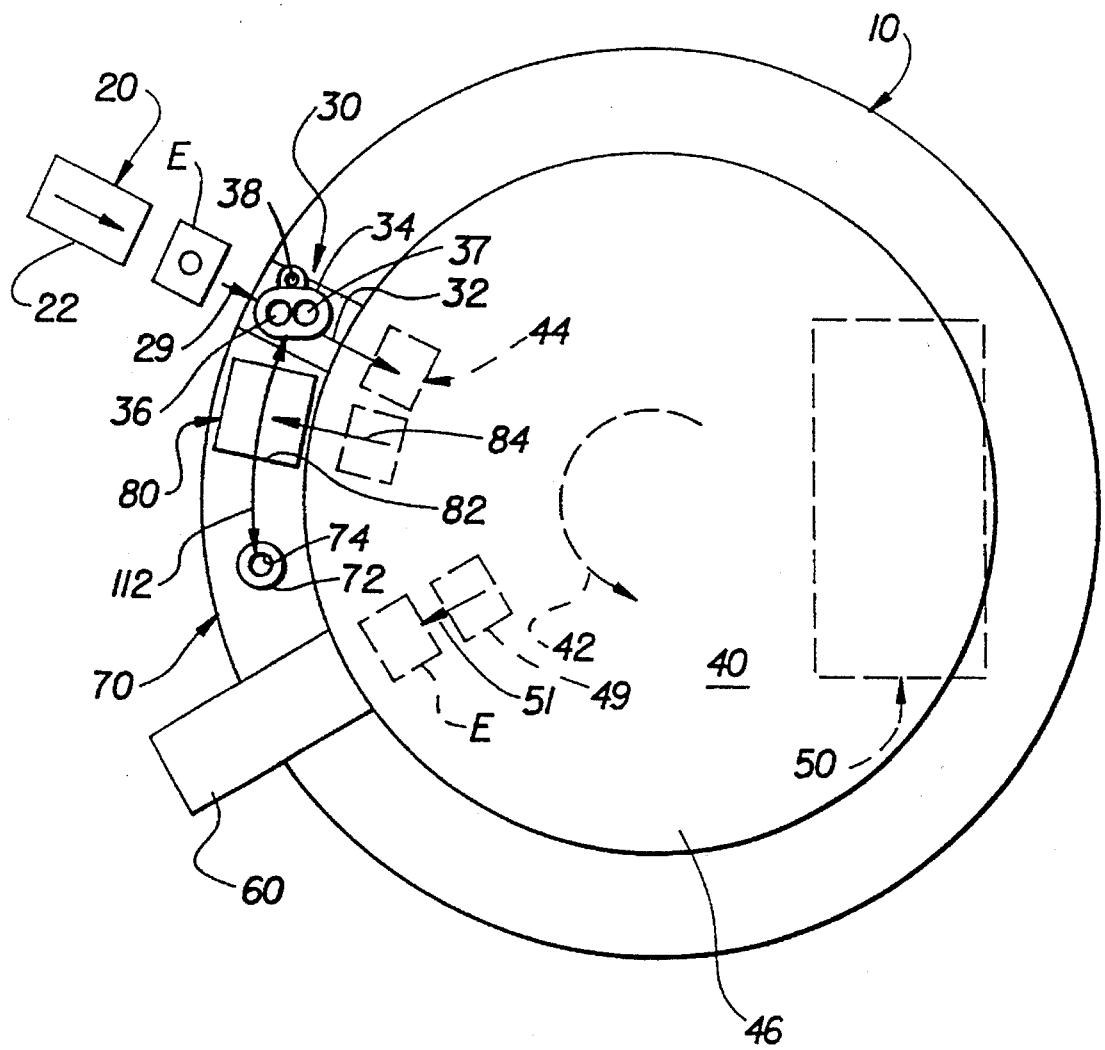
FIG. 1 is a partially schematic, plan view of an analyzer which is particularly useful in accordance with the present invention.

Referring to FIG. 1, an analyzer 10 useful for the method of the present invention described herein includes a station 20 for loading a slide-like test element E into a sample dispensing station 30, and for loading such an element E, along a path 32, now bearing patient sample, into an incubator 40. Preferably loading station 20 includes a pusher blade 22 that pushes the element E along a path 29 so as to be injected into dispensing station 30. The loading apparatus includes a tip locator 34 having apertures 36, 37 as is conventional for patient sample metering, and an aperture 38, for reference liquid metering, as is also conventional.

Figure 2:
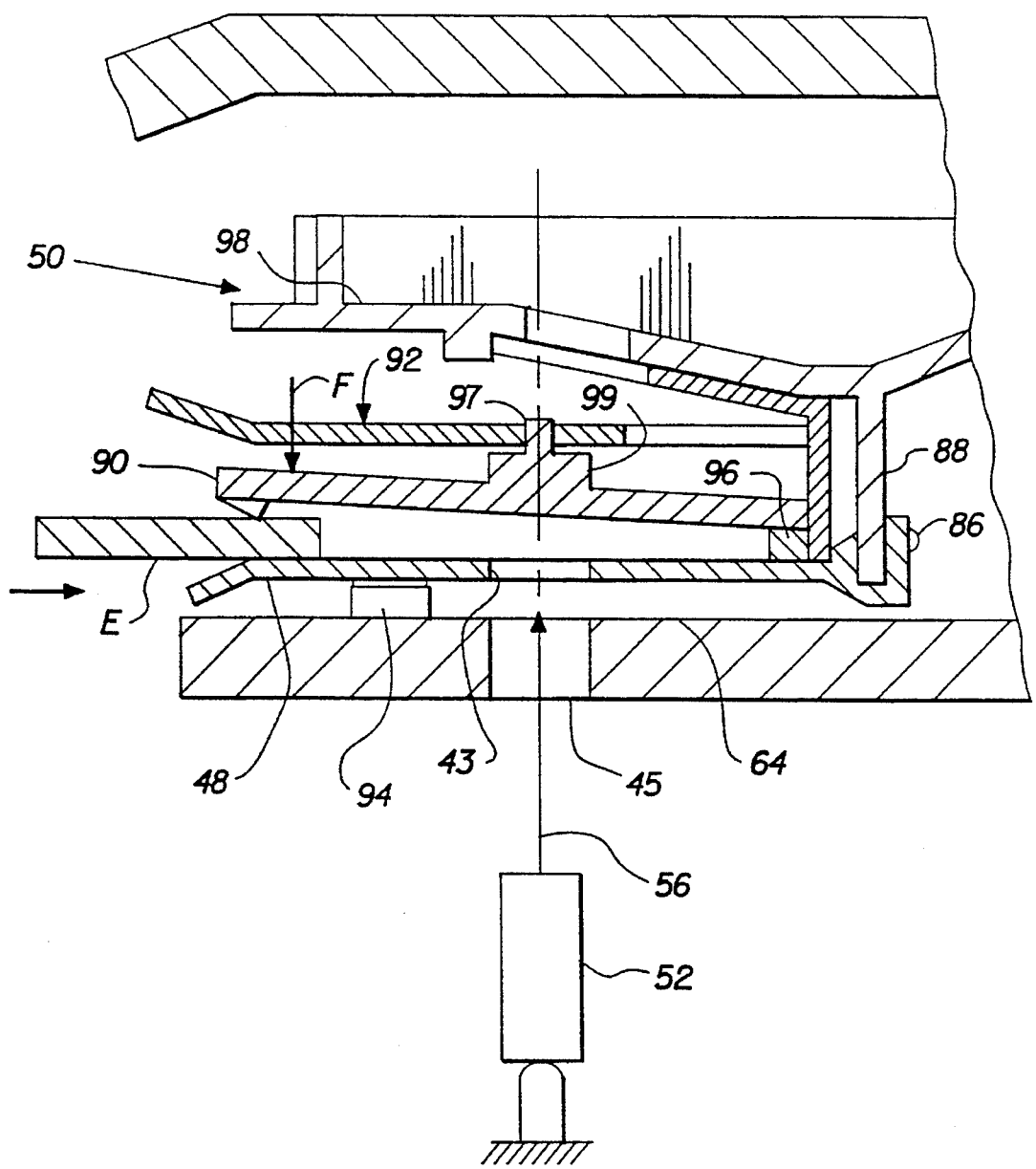
FIG. 2 is a side elevational view of the read station of the analyzer depicted in FIG. 1.

Also preferably, incubator 40 is the rotating type, having movement about a central rotational axis, as per arrow 42, and includes an optical reflectometer 52, FIG. 2, for scanning colorimetric test elements disposed at a read station 50, FIG. 1, while the elements are individually held at a plurality of stations 44, as defined by a rotor 46. A viewing aperture 43, FIG. 2, is centrally located within each station 44 to be aligned with a held slide element E to be read by the reflectometer 52 at read station 50. Analyzer 10 also includes an electrometer 60 for reading potentiometric test elements after they are removed from incubator 40 by a second pusher blade 49. A wide variety of incubators capable of receiving both colorimetric and potentiometric type test elements are known and are useful for this purpose, for example, the incubator described by U.S. Pat No. 5,037,613.

Still referring to FIG. 1, a wash station 70 is disposed outside of incubator 40, and is displaced circumferentially from the sample dispensing station 30. Wash station 70 comprises a boss 72 and aperture 74 that serves to hold a dispensing tip (not shown) in proper orientation with respect to a test element to be washed. Positioned between stations 70 and 30 is an eject station 80 including a discharge path defined by aperture 82 into which a test element is ejected, arrow 84, when its readings have been completed.

Figure 3:
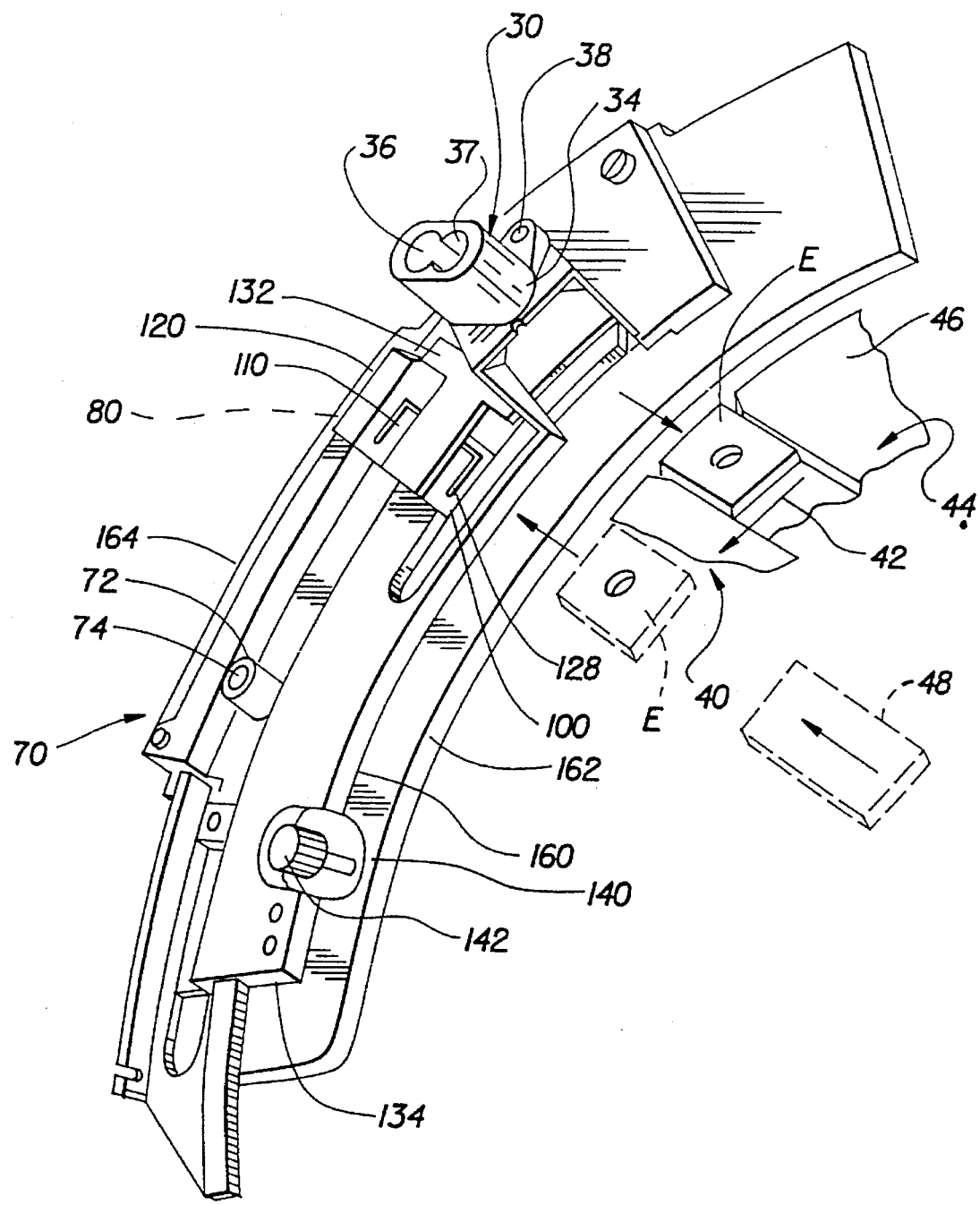
FIG. 3 is a fragmentary perspective view of the analyzer of FIG. 1 showing in particular a shuttle apparatus useful for conveying a slide element from and to an incubator to and from a wash station.

Referring briefly to FIG. 3, a shuttle apparatus 100 is provided to allow test elements to be intercepted at the eject station 80, taken to wash station 70, and reinserted into the incubator 40. Shuttle apparatus 100 comprises a catcher plate 110, means 160 for supporting the catcher plate 110 for movement along a preferably curvilinear path 112, FIG. 1, and means 140 for driving the catcher plate 110 along path 112 so that a test element E washed at station 70 can be reinserted. A more detailed description of this apparatus follows. Note that for clarity, the shuttle apparatus 100 is not shown in FIG. 1.

Referring now to FIG. 2, the supporting of test elements within an incubator 40 and the read station 50 will be described in greater detail.

Incubator 40 comprises a lower stationary surface 64 and the rotor 46, FIG. 1, which includes a rotatable support 48, a cover member 90 and a spring 92 which biases the cover member towards the lower support with a spring force F, for holding element E therebetween. Element E is shown in the Figure as being fed into a rotor station 44, FIG. 1. Lower support 48 is preferably structurally defined as a ring attached by suitable means, such as a screw 86 to a flange 88 of the rotor 46, FIG. 3. The ring-like support 48 is placed in sliding contact against three stationary reference pads 94 (only one of which is shown) adjacent to read through aperture 43 which passes through the lower stationary surface 64 as well as the rotatable support 48. Cover portion 90 prevents premature evaporation of sample from a test element, as is conventional. The shape of the cover and that of the spring are not important, other than the cover must allow the slide element E to be pushed into and out of a station 44, FIG. 1, as herein described.

In the embodiment shown, the spring 92 is mounted so as to be releasably captured or sandwiched between an upper rotor portion 98 that extends out over much of station 44 as well as the cover portion 90. Portion 98 bears directly onto cover member 90, specifically a boss 99 thereof, which has a pin 97 to penetrate a portion of the spring 92. The cover can include a foot 96 to raise the cover slightly above an incoming element E, whereby any liquid on the element, is not wiped against the cover member. Additional details relating to the positioning of the element E in a conventional incubator, including the use of the reference pads 94, are described in the previously referenced U.S. Pat. No. 5,037, 613.

In order to allow test elements to be read while sandwiched between the rotatable support 48 and cover member 90 of rotor 46, the reflectometer 52 at read station 50 is fixed relative to the stationary lower surface 64 of incubator 40, for example, below it. Reflectometer 52 is therefore disposed as shown in FIG. 2 and includes a light source, which emits an optical beam 56. An aperture 45 is defined in the lower stationary surface 64 which allows the passage of the emitted beam 56. Similarly, aperture 43, provided through rotatable support 48, also allows the optical beam 56 emitted from the reflectometer 52 to pass therethrough and impinge on an element E, as is conventionally known. See FIG. 4. Apertures 43, 45 are also shaped to allow a reflected beam (not shown) to pass to a detector, (not shown), at a different angle than optical emitted beam 56 (for example, 45 and 90 degrees, respectively, to the surface of element E, see FIG. 4). As noted above, the details relating to the operation of optical reflectometers in general are commonly known and do not require additional discussion.

Referring now to FIG. 3, a more detailed description of the shuttle apparatus 100 follows. Catcher plate 110 is preferably defined by a frame 120 to hold an ejected test element E at one side within a support member 128 which is preferably cantilevered to frame 120 so that it can flex. Catcher plate 110 is connected to a drive tongue 132 which extends substantially along the curvature of path 112, FIG. 1, having a rack 138 along one inside raised edge 134 which is driven by a gear 142.

The catcher plate 110 and drive tongue 132 are supported between two arcuate track members 162, 164, each having the same general curvature and thereby defining the path 112. Additional details relating to the construction of the shuttle apparatus 100 can be found in commonly assigned U.S. Pat. No. 5,174,960, which is hereby incorporated by reference.

Figure 4:
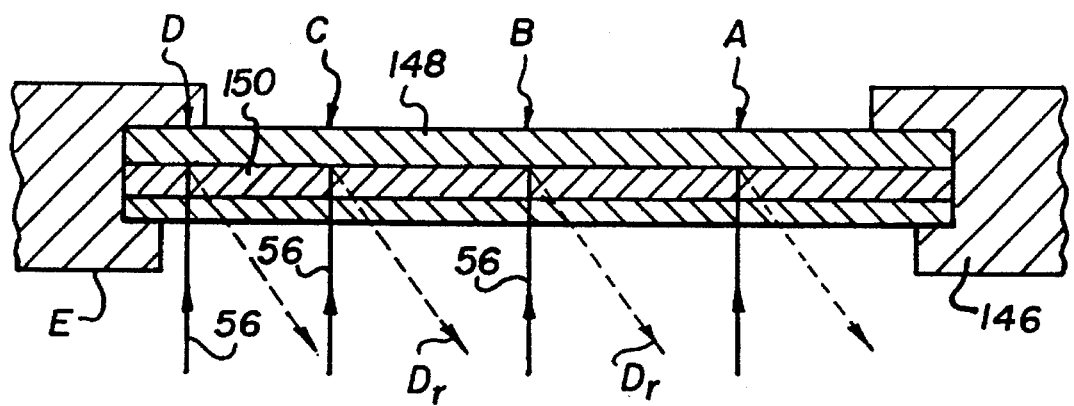
FIG. 4 is a partial side elevational view, taken in section of a slide test element used by the apparatus shown in FIGS. 1–3.

The operation of the invention can now be described according to the drawings. Referring to FIG. 4, a dried chemistry test element E used in the above described apparatus includes a supporting frame portion 146, a chemistry or reagent portion 148 which is substantially centrally disposed as shown on the supporting frame, and a porous spreading layer 150. A typical colorimetric test element is described in greater detail in commonly assigned U.S. Pat. No. 3,992,158, issued to Przybylowicz, et al which is hereby incorporated by reference.

The element E shown in FIG. 4 has already had a quantity of sample fluid substantially centrally dispensed in the form of a droplet at dispensing station 30 by conventional means through tip locator 34. Pusher blade 22 then pushes by known drive means (not shown) the element E into the incubator 40 and specifically into a station 44 of rotor 46, to be initially incubated for a predetermined period. Following this incubation, element E is pushed out of incubator 40 by pusher blade 48, FIG. 3, and onto the catcher plate 110 where the element is conveyed to the wash station 70. Here, a pipette tip (not shown) placed within the aperture 74 dispenses a quantity of wash liquid, typically about 12 microliters of a hydrogen peroxide solution additionally comprising an electron transfer agent (ETA) e.g., 4'-hydroxyacetanailide, a stabilizer e.g., diethylanitriaminopentacetic acid, and a cationic surfactant in a buffer, e.g., a phosphate buffer, such as described in U.S. Ser. No. 994,851 filed 22 Dec. 1992, now abandoned, onto element E.

In a preferred embodiment the wash liquid is added to the element E at a position designated as A which is between the periphery of the wetted sample having a typical diameter of about 11 mm and the center of the sample droplet, see FIG. 4. Element E is then shuttled back to the input station 30 and is reinserted into an incubator rotor station 44 via the pusher blade 22.

Rotor 46 rotates, per arrow 42, by known and conventional drive means, such as a stepper motor (not shown) until the station 44 having the element E disposed therein is positioned at read station 50 and the apertures 43, 45 are aligned with the reflectometer 52 to make an "on-center" read; that is, an optical density reading ($D_r$) corresponding to substantially the center of the area defined by the wetted sample, as represented pictorally in FIG. 4 by position B.

According to the present invention, it is desirable to offset the test element in order to make comparative readings. Shifting or relocating of the element E within the read station 50 is required due to the capability and functional requirements of the reflectometer 52. Therefore, referring to FIGS. 4, 5 and 6, means are shown for relocating or offsetting a slide element E within a station 44 of the incubator rotor 46 so that an "off-set" or "off-center" reading can also be made at read station 50, preferably at position C, which, FIG. 4, is a location along the chemistry portion 154 of the element E which is aligned directly opposite from the wash site: position A.

Figure 5:
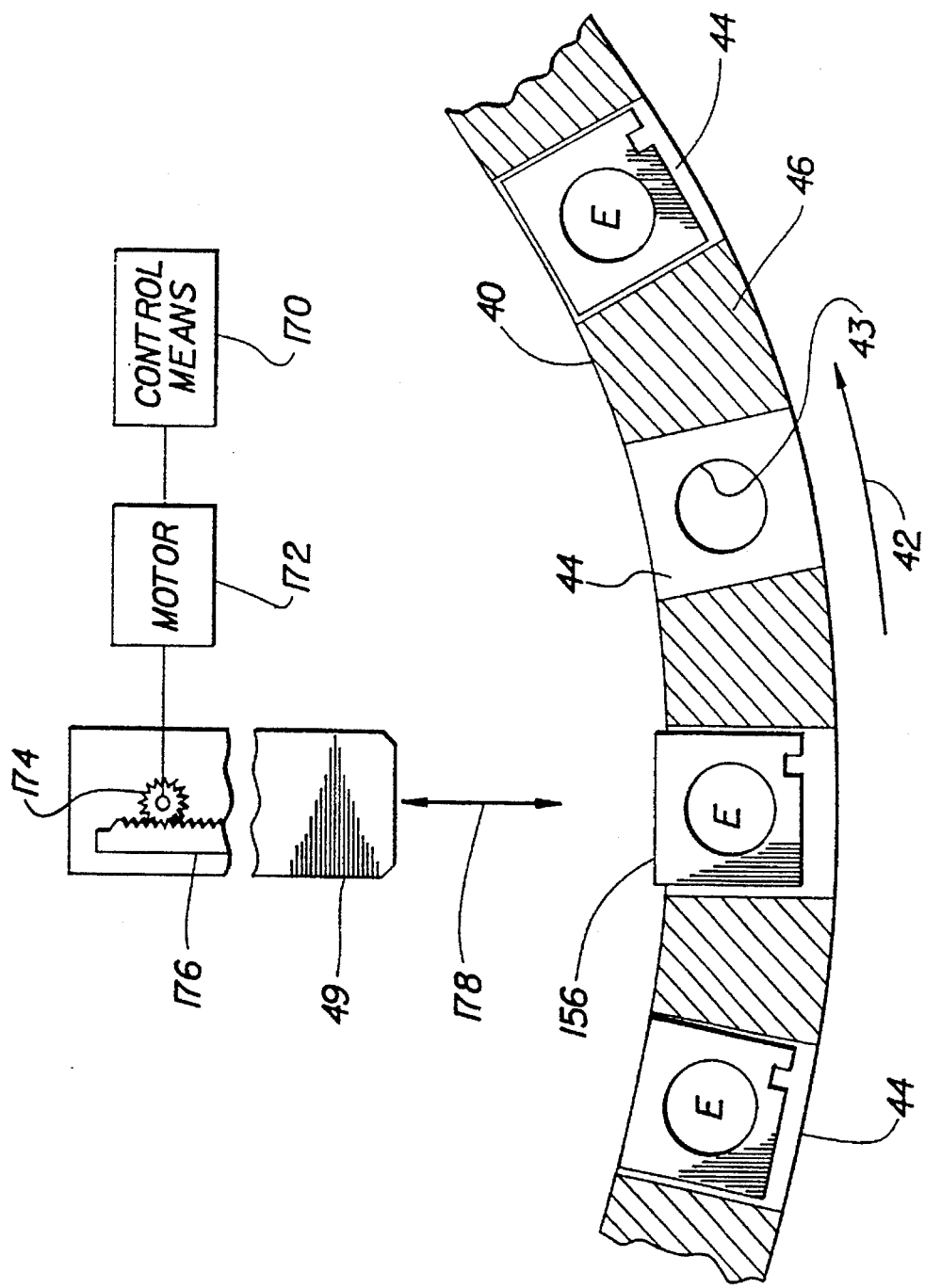
FIGS. 5 and 6 are partial top perspective views of means for shifting the position of a slide element within the incubator of the analyzer of FIG. 1 so that the element may be read at an off-center position.

In a first means depicted in FIG. 5, a pusher blade 49 is provided within the periphery of the incubator rotor 46. Pusher blade 49, is ordinarily useful in delivering an element E from station 44 to a read station adjacent the electrometer 60. In this particular embodiment pusher blade 49 is driven in a radial direction, as shown by arrow 178 and by known means, such as a stepper motor 172, control means, such as a microprocessor 170 and a shuttle mechanism 174, that is capable of incrementally advancing the element E a very short distance, preferably 2–3 millimeters in the radial -y- direction. After element E has been shifted to the off-center position, rotor 46 is rotated, per arrow 42, until element E is aligned with the read station 50. At read station 50, element E will then be positioned relative to apertures 43, 45 and to the reflectometer 52 so that the light beam will impinge upon the element E at position C, FIG. 4, rather than the typically centered position B, FIG. 4.

According to the present invention, an on-center read can first be performed on an element E at the read station 50. The element E can then be offset by rotating the rotor 46 until the designated element E is aligned radially with the pusher blade 49. Using the described shuttle mechanism 174 and stepper motor 172, the pusher blade 49 can contact side edge 156 of the element E and shift the element E by a predetermined distance within a station 44. Thereafter, the rotor 46 can again be rotated, per arrow 42, until the element E is aligned with the read station 50 so that an off-center read can be made. Subsequently, if desired, the incubator 40 can be rotated such that pusher blade 22 can realign the element E into a substantially centered position within station 44. The particular ordering of the above events are not necessarily limited such that an off-center read can be made prior to a centered read of a particular element E.

Figure 6:
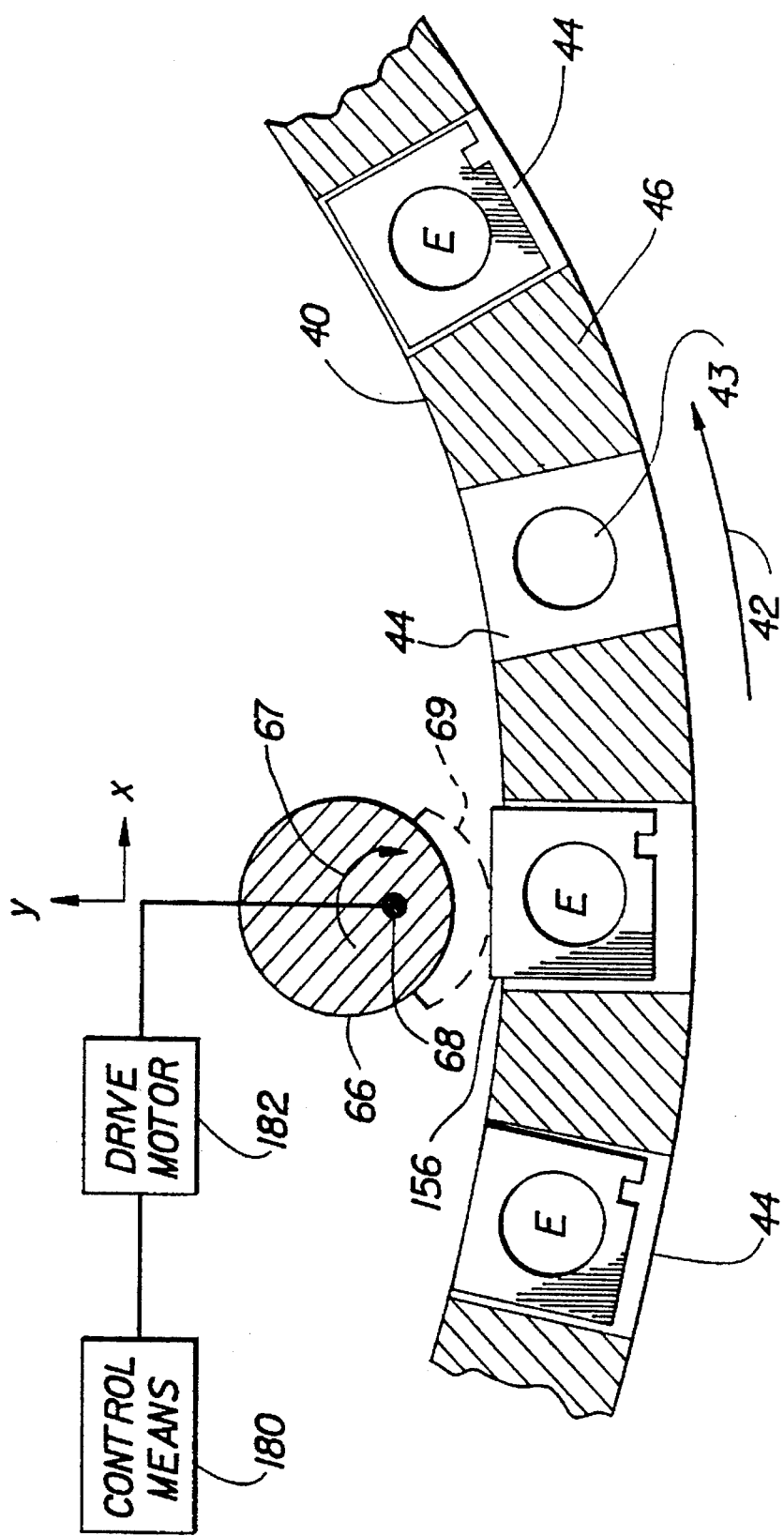

It can readily be seen that the element offsetting means need not be limited to a pusher blade, as previously described, provided that any means used advances element E a particularly small radial distance within a station 44. For example, and referring to FIG. 6, a roller 66, or other camming means, is mounted in a preferably eccentric position on a rotatably driven shaft 68 which is positioned within the interior periphery of the incubator 40. The shaft 68 can be driven conventionally, such as by a drive motor 182 having a control means 180, such as a microprocessor. Roller 66 has a generally cylindrical sidewall 69 which contacts element E most preferably at the middle of its trailing side edge 156 to prevent cocking of the element E. A more detailed description of the described offsetting means illustrated in FIGS. 5 and 6 is provided in commonly assigned U.S. Pat. No. 5,196,168, entitled: INCUBATOR WITH POSITIONING DEVICE FOR SLIDE ELEMENTS by Muszak, et al, issued Mar. 23, 1993, the contents of which are hereby incorporated by reference.

Either of the above means allows the slide element E to be repositioned within the rotor station 44 relative to the read station 50. In this way, the element E can be read at a non-center location so that a density reading can be taken which can be compared with a center location density result.

It should be readily apparent that the method herein described can also be easily applied to verify a centrally applied wash such as by first using the reflectometer 52 to measure at an "on center" location and then incrementing the element E in a manner as described to measure at an "off-center" location to provide comparative data for verifying a particular washing operation.

Analysis: The rationale for providing comparative data will now be explained. It will be readily apparent that the (reflection density or optical density) $D_r$ or rate $D_r$ value, as measured at an off-center site oppositely situated from the wash site, should be at a minimum substantially equal to or appreciably greater than a $D_r$ reading taken at the center of the detection read area of an element E if the wash process is adequate to displace unbound label horizontally through the spreading layer of the slide element. A quantitative measure, therefore, in accordance with the present invention, can be made to verify the adequacy of the wash process, reducing the number of errors which could occur therefrom.

In assessing the relative success or failure of a particular wash operation in a competitive assay where analyte competes with a labeled analyte binding to an immobilized analyte-binding reagent, the results obtained according to the method described herein can be generally grouped within three possible sets of results, summarized as follows:

(1) If the optical density ($D_r$) or rate $D_r$ as measured by the reflectometer 52 is higher at the centered read area (position B) than at an off-center site (position C), beyond normal noise variability differences, then there has been an insufficient wash volume displaced beyond the centered read area. This indicates little or possibly no density development has occurred in the off center site and unbound material remains in the read detection area. In other words, a too small volume of wash liquid has been dispensed to element E. The analyzer is sent a signal to discard the test element and its results, and they are discarded. The patient sample is retested with a new slide test element.

(2) If the optical density reading or rate $D_r$ at the off-center read site (position C) is higher or equal to that at the center read area (position B), then unbound label has been effectively displaced across element E AND the sample has a high level of the analyte in question. This indicates an adequate wash volume has been dispensed and displaced and provides verification of the wash process.

(3) Finally, if optical density or rate readings taken at the first and second read positions (positions B and C as per above) are substantially equal and both readings are low, that is are less than about $0.2 D_r$ or in rate $D_r$ terms lower than the lowest calibrator rate, this strongly indicates that there has been an insufficient wash volume to penetrate the centered read area (position B). As in 1) above, the test element and its results are discarded and the test is redone.

Figure 7:
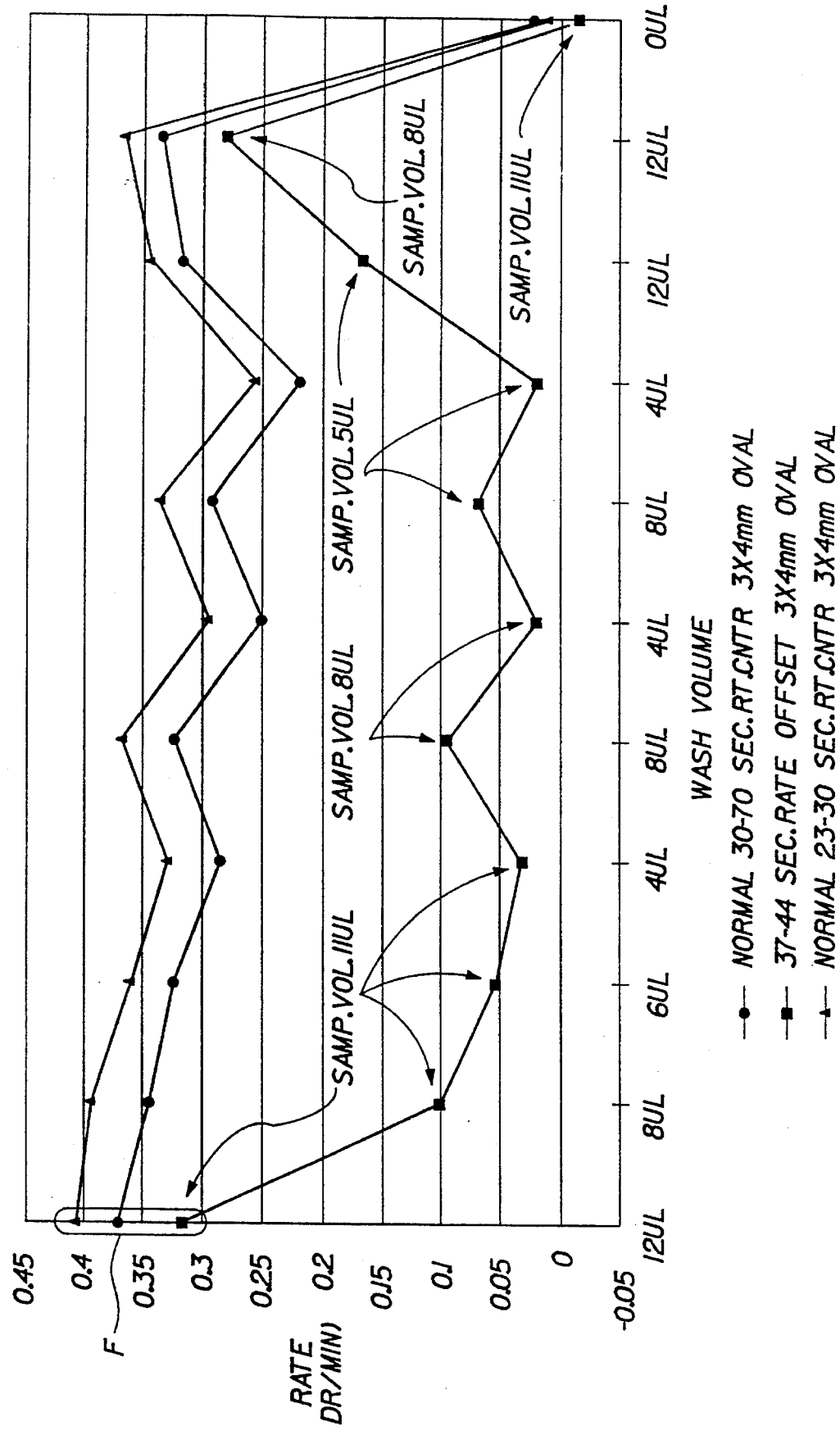
FIG. 7 is a graphical representation of optical density test results as compared at specific locations along a washed slide element.

Referring now to FIG. 7, a graphical representation of data is provided for a series of optical density readings taken at positions B and C for an element E that has been washed at position A, as well as data obtained for a centrally washed element at positions B and C.

A series of analytical elements (slides) for assay of phenytoin were employed in this example. The slides comprised a transparent poly(ethylene terephthalate) support coated with a hardened gelatin layer having a buffer, surfactant, and an electron transfer agent; a receptor layer having an immobilized antibody for binding phenytoin in a binder; and a porous polymer particle spreading layer having polymer particles, a binder, a leuco dye, buffer, and surfactant, and gravure printed thereon, a thin deposit comprising a buffer, an electron transfer agent, and a label, said label being phenytoin having amine-enriched horseradish peroxidase bound thereto via an extended linking group. The coating was cut and mounted as slides.

A human-based serum solution containing 1.94 g/mL of phenytoin as an analyte and 0.1 g/mL of protein was provided for testing to generate the data in the accompanying figure. A wash solution comprising hydrogen peroxide, phosphate buffer, an electron transfer agent and a stabilizing agent was prepared for use in the wash step of the assay process.

The assay process comprised the steps of:
1. Spotting a slide with analyte solution in the amount (in μL) indicated in the Figure,
2. Incubating the slide at 37° C. for 5 minutes,
3. Washing with the wash solution by applying it to the slide at a position about 3.2 mm from the center of the point of application of the analyte; this corresponds to position A from the preceding discussion.
4. Reading the reflection density ($D_r$) at 670 nm at 37° C. at the center of the spot (position B) and at a position offset 2 mm from the center of the spot oppositely from position A=position C. The on-center readings were made at 23 and 30 seconds after the beginning of the wash, and the off-center readings were made at 37 and 44 seconds after the beginning of the wash. The density rates ($d_r$/min) were calculated by dividing the difference in densities read by the time between readings (7 sec), and were plotted versus the wash volume for the series of assays. The results for the series of assays using the same amount of analyte and different amounts of wash solution and sample volumes are provided in the figure. Note that the off-center readings are taken later in time than the on-center readings. Extrapolation of the off-center readings back to the time of on-center readings would result in the off-center $D_r$ being higher than the on-center $D_r$ in the case where there is adequate wash volume. See point F designated in FIG.7.

The data shows that the process can detect either of two defects: (1) too low a sample volume and (2) too low a wash volume. Where the sample and wash volumes are both the proper amounts, e.g., 11 and 12 μL, respectively, the on-center and off-center rates are very close to each other, and are quite high. If the sample volume is proper, but there is no wash, the on- and off-center rates will still be close to each other but will be very low, i.e., near zero. Under any other conditions, e.g., (1) where the sample volume is correct but the wash volume is low, e.g., 4 μL, (2) where the wash volume is correct but the sample volume is low, e.g., 5 μL, or (3) where the sample volume and wash volume are both low, e.g., 5 and 4 μL, respectively, there is a considerable difference between the on-center rate and the off-center rate. These phenomena occur as the wash volumes are lowered because there is inadequate transport of unbound analyte and signal reagents by the off-center wash. For small sample volumes, the rate is very low in regions where the chemistry was still dry before wash since there was insufficient time for binding of analyte or enzyme-labeled analyte to the antibody beads to occur, even if the sample fluid is transported over this region during wash.

The invention has been described in detail with particular reference to preferred embodiments thereof, for example, it is readily apparent that the wash operation could take place by dispensing wash liquid at the centered read area, such as known and described in U.S. Pat. No. 4,517,288, among others. In this case, the first read position and the first wash position are coincident and the second read position can be an outer radial position of the detection read area. Other similar variations and/or modifications can be effected within the scope of the invention. For example, a CCD array (not shown) or reflectometer having two or more read positions can be provided for the reflectometer 52, thereby allowing element E to be scanned without having to move element E to an off-center position for scanning.

As still another alternative, the reflectometer 53 is typically equipped with a read sync to allow radial orientation shifts of a station 44. This feature can be used to provide comparative data for a test element E. In order to use this technique, however, the element must be oriented by 90 degrees so that a line taken through each of the positions A, B, and C extend in an -x- direction, see FIG. 5, rather than a typical -y- orientation. By rotating the element E in this manner and then using the read sync to make a slightly offset radial read on the element an off-center detection can be made. In other words, the wash could be performed at 90 degrees from the position shown in FIG. 5.

Additional Embodiments

Additionally, it is possible to utilize the present invention in a dual wash situation, wherein the first wash is only an inert liquid, such as water, and the second wash includes activator solutions, such as hydrogen peroxide. (Splitting the wash step into 2 steps, one without an activator solution, is known in the art.) In such a case, the detection of an adequate wash is not done by detecting, after the first wash, a "ring" of density formed at the read location "B", because no color, in ring form or otherwise, will form in the absence of an activator solution. If detection of the first wash is desired nevertheless, a mobile magenta dye is preferably incorporated, since no color formation is possible otherwise. To detect the magenta dye having been washed by the first wash, detection is done at "C". After the second wash, detection is preferably done at "D", FIG. 4, to detect that that dye has now moved to "D".

The dispensing of the 2 washes in a dual wash process is preferably done both at the same location, such as "A" or "B", FIG. 4. Alternatively, as described and claimed in commonly owned application U.S. Ser. No. 08/470,100 filed by Merrit N. Jacobs on Jun. 6, 1995 entitled "Washing at Different Locations" (Docket No. 69635), the locations of the wash can be split so that a portion is dispensed at "A" and a portion at "B".

What is claimed is:

1. A method for verifying a proper washing sequence on a plurality of test elements having a chemistry portion of at least one reagent layer disposed thereon, the method comprising the steps of:

a) adding a wash liquid to each of said test elements at a first wash position located within said chemistry portion;

b) reading each of said test elements at a first read location located within said chemistry portion to detect a wash-influenced result;

c) reading each of said test elements at a second read location within said chemistry portion that is different from said first read location, to detect a wash-influenced result, one of said first and second read locations being within said first wash position;

d) comparing the readings of steps b) and c); and e) discarding the results of the test if said reading of step b) is higher than said reading of step c) beyond normal noise variability.

2. A method as claimed in claim 1 in which step b) further comprises the step of reading said element at substantially a center of said wash position and step c) comprises reading said element at a location removed from said center of said wash position.

3. A method as claimed in claim 2 further comprising the step of applying a wash-activable coating at said removed location prior to said washing step a), wherein said coating produces a detectable signal when wetted.

4. A method as claimed in claim 1, wherein step a) comprises the step of applying wash liquid at a position located removed from the center of said chemistry portion.

5. A method as claimed in claim 1, wherein said step a) comprises adding wash liquid at an off-center location along said chemistry portion, step b) comprises reading said test element at the center of said chemistry portion and step c) comprises reading said test element at a location which is radially opposite said wash position, relative to said center of said chemistry portion.

6. A method as defined in claim 1, wherein said step a) comprises adding two wash liquids, one after the other, to either the same or a different respective location on the test element, the first of said wash liquids comprising water without any activating solution.

* * * * *